US00PP30596P3

(12) United States Plant Patent
Wells

(10) Patent No.: US PP30,596 P3
(45) Date of Patent: Jun. 25, 2019

(54) *HYDRANGEA* PLANT NAMED 'MONPULSEL'

(50) Latin Name: *Hydrangea aspera*
Varietal Denomination: MONPULSEL

(71) Applicant: Richard Wells, Dayton, OR (US)

(72) Inventor: Richard Wells, Dayton, OR (US)

(73) Assignee: Monrovia Nursery Company, Azusa, CA (US)

( * ) Notice: Subject to any disclaimer, the term of this patent is extended or adjusted under 35 U.S.C. 154(b) by 15 days.

(21) Appl. No.: 15/731,676

(22) Filed: Jul. 13, 2017

(65) Prior Publication Data

US 2019/0021200 P1 Jan. 17, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
See application file for complete search history.

*Primary Examiner* — Anne Marie Grunberg
(74) *Attorney, Agent, or Firm* — Cassandra Bright

(57) ABSTRACT

A new and distinct *Hydrangea* cultivar named 'MONPULSEL' is disclosed, characterized by broad foliage which is noticeably thicker and more rigid than typical. Plants are strongly upright with compact growth. Branching is excellent, with strong branches produced, holding inflorescences at a more upright position. The new variety is a *Hydrangea*, normally produced as an ornamental plant for containers or gardens.

3 Drawing Sheets

Latin name of the genus and species: *Hydrangea aspera.*
Variety denomination: 'MONPULSEL'.

BACKGROUND OF THE INVENTION

The new *Hydrangea* cultivar is a product of a breeding program under the direction of the inventor, Richard Wells, a at a commercial nursery in Dayton, Oreg. The new variety was selected among a planting of seedlings of *Hydrangea aspera* 'Plum Passion', unpatented.

Seed was bulk collect from unpatented *Hydrangea aspera* 'Plum Passion' plants. The new variety was selected among a planting of these seedlings in May 2013.

First asexual reproduction of the new cultivar 'Monhinschf' was performed by softwood vegetative cuttings at a commercial laboratory in Dayton, Oreg. in August of 2013. Four generations have been produced, and have shown that the unique features of this cultivar are stable and reproduced true to type in successive generations.

SUMMARY OF THE INVENTION

The cultivar 'MONPULSEL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MONPULSEL' These characteristics in combination distinguish 'MONPULSEL' as a new and distinct *Hydrangea* cultivar:

1. Excellent branching.
2. Strongly upright and compact growth habit.
3. Strong branches hold inflorescence more upright.
4. Foliage which is noticeably thicker and more rigid.
5. Broad foliage.

PARENT COMPARISON

Plants of the new cultivar 'MONPULSEL' are similar to plants of the parent, in most horticultural characteristics, however, plants of the new cultivar 'MONPULSEL' differ in the following:

1. The new variety produces stronger branches, resulting in a sturdier plant that does not flop open.
2. Plants of the new variety are more upright and compact.
3. Foliage of the new variety is thicker and more rigid, as well as wider.
4. Flowers of the new variety are held more upright, due to stronger branches.

The parent variety was self-crossed, there is only one parent.

COMMERCIAL COMPARISON

'MONPULSEL' can be compared to the patented commercial variety *Hydrangea aspera* 'Hot Chocolate', unpatented. These varieties are similar in most horticultural characteristics; however 'MONPULSEL' differs in the following:

1. The comparator produces darker pink flowers than the new variety.
2. Plants of the new variety are approximately ½ the height of plants of this comparator.

BRIEF DESCRIPTION OF THE PHOTOGRAPHS

The accompanying photograph in FIG. 1 illustrates in full color a typical plant of 'MONPULSEL'grown in a field, in Dayton, Oreg. USA. Age of the plant photographed is approximately 3 years.

Figure 1:
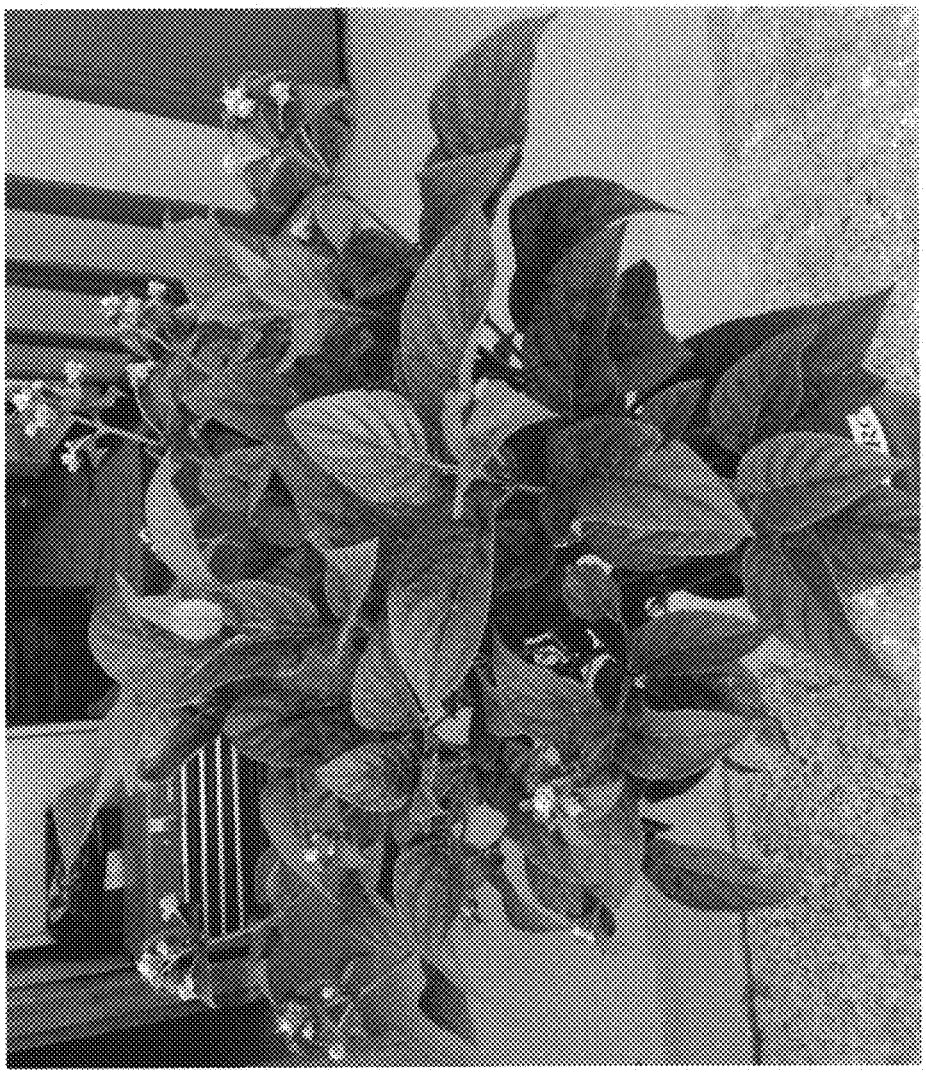
Figure 2:
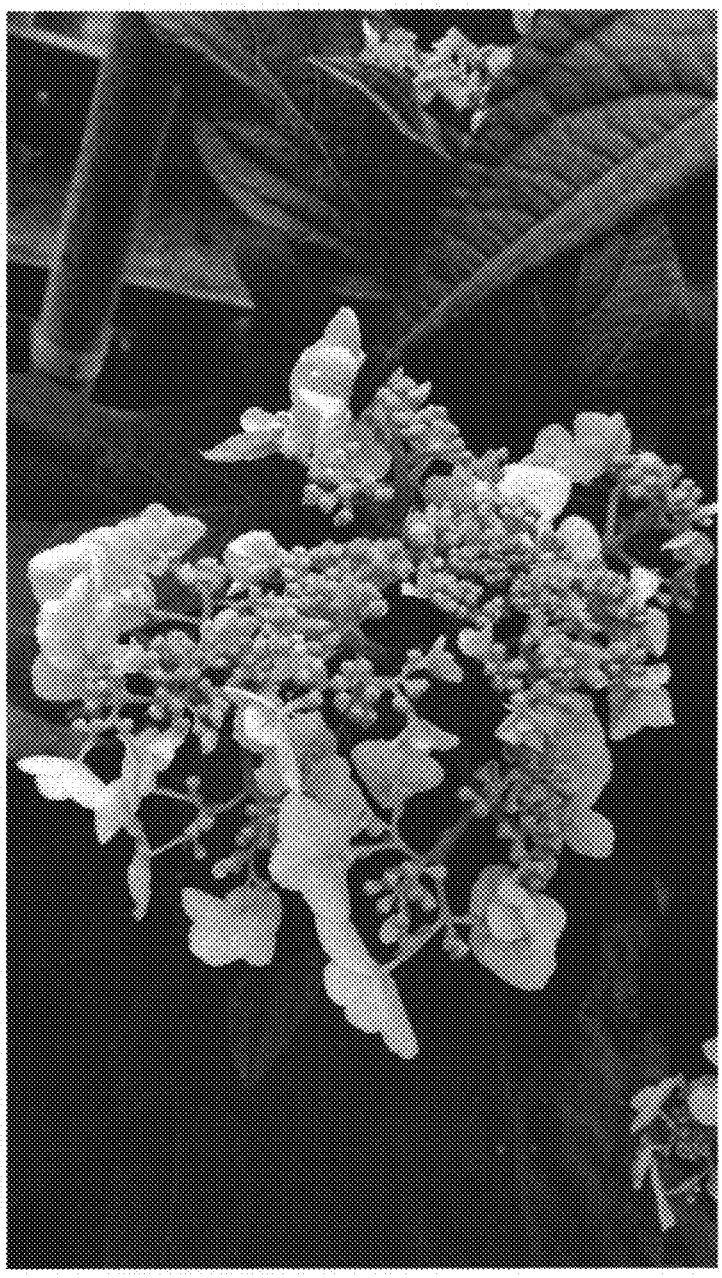
FIG. 2 illustrates typical foliage and inflorescence of the new variety.
Figure 3:
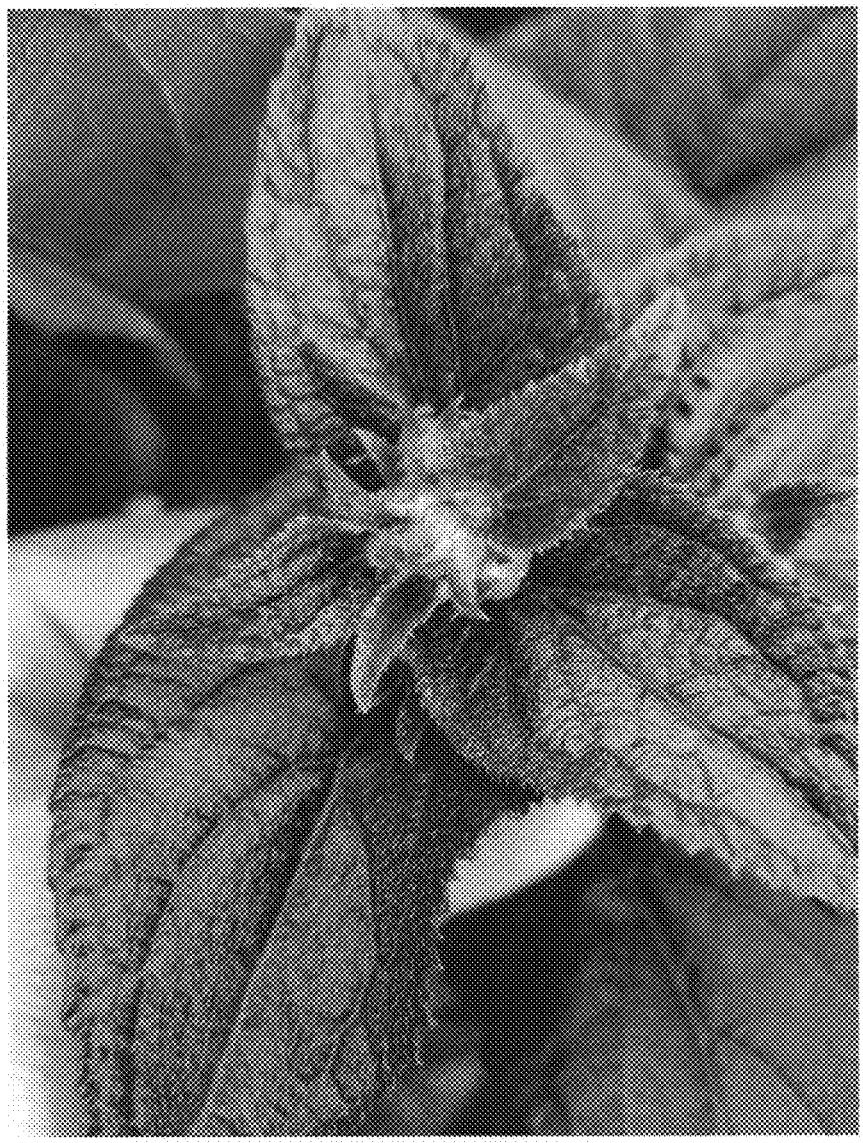
FIG. 3 illustrates new growth of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2015 Royal Horticultural Society Colour Chart except where general terms of ordinary dictionary significance are used. The following observations and measurements describe 'MONPULSEL' plants grown in a field, in Dayton, Oreg., USA. The growing temperature ranged from approximately 18° C. to 27° C. daytime and 5° to 10° C. at night. Measurements and numerical values represent averages of typical plant types. Measurements were taken during June of 2017.

Botanical classification: *Hydrangea aspera* 'MONPULSEL'.

PROPAGATION

Time to initiate roots: Approximately 18 days at approximately 24° C.

Time to produce a rooted young plant: Approximately 60 days at approximately 24° C.

Root description: Thin to thick, moderate to dense, freely root branching, fleshy. Color is white and brown.

Propagation method: Softwood cuttings.

PLANT

Age of plant described: 1 to 2 years.

Pot size: 5 gallon.

Growth habit: Upright flowering perennial shrub, or subshrub.

Overall plant shape: Upright V-shape.

Height: 50 cm.

Plant spread: 75 cm.

Growth rate: Rapid.

Plant vigor: Good.

Branching characteristics: Upright/outward basal branches, some pinching required.

Length of lateral branches: 20 to 35 cm.

Number of lateral branches: 4 main branches at base of plant, breaking into 2 to 4 lateral branches.

Diameter of lateral branches: 7.5 mm.

Lateral branch shape: Rounded.

Lateral branch strength: Moderately flexible, breakage can occur.

Internode length: Average range 8 to 12 cm.

Branch color: Immature: Near RHS Yellow-Green 148A, covered in Greyed-Purple 187A and N187A. Mature: Near RHS Grey-Brown 199A.

Branch aspect: 10-25°.

Branch texture: Mature branches scaly. Immature branches moderate coverage of very short pubescence, intermediate branches (between mature and immature) nearly glabrous, infrequent sparse pubescence. No lenticels.

Foliage:

Leaf:

*Arrangement.*—Opposite.

*Average length.*—Average range 15 to 25 cm.

*Average width.*—Average range 6 to 10 cm.

*Shape of blade.*—Deltoid, oldest foliage nearly cordate.

*Apex.*—Short acuminate, aspices approximately 2 mm, not sharp.

*Base.*—Obtuse to cordate.

*Margin.*—Serrate to crenate.

*Texture and appearance of top surface.*—Rugose, leathery.

*Texture and appearance of bottom surface.*—Leathery, prominent veins.

*Leaf pubescence.*—Occurs on upper and lower surfaces, sparse along veins.

*Color.*—Young foliage upper side: Near RHS Greyed-Purple 183C, vein area flushed near Yellow-Green 147A. Young foliage under side: Near RHS Greyed-Purple 185C. Mature foliage upper side: Between RHS Greyed-Green N189A and Yellow-Green 147A. Mature foliage under side: Near RHS Greyed-Purple 186A.

*Venation.*—Type: Pinnate. Venation color upper side: Near RHS Greyed-Purple 186A. Venation color under side: Near Greyed-Purple 186A.

Petiole:

*Average length.*—3.0 to 4.0 cm.

*Diameter.*—3.5 to 5.0 mm.

*Color.*—Upper side: Near RHS Greyed-Purple N186C.

*Under side.*—Near Grey-Brown N199A.

*Texture upper side.*—Short hirsute.

*Texture under side.*—Short hirsute.

FLOWER

Bloom period:

*Natural season.*—Begins flower mid-Summer, lasts about 4 weeks.

Inflorescence:

*Type.*—Small, clustered lacecap.

*Quantity of flowers per inflorescence.*—Fertile flowers: 10 to 20. Sterile Flowers: Average 7 to 12.

*Persistent or self-cleaning.*—Persistent.

*Fragrance.*—Mild and slightly sweet.

Panicle:

*Shape.*—Irregular oblong.

*Height.*—5 cm.

*Diameter.*—3.5 cm.

Sterile flower:

*Bud shape.*—Orbicular.

*Bud length.*—4 mm.

*Bud diameter.*—3 mm.

*Bud color.*—Near RHS Red-Purple 65D.

*Flower aspect.*—Outward.

*Flower shape.*—Irregularly round.

*Flower length.*—Average 1.0 cm.

*Flower diameter.*—Average 1.0 cm.

*Flower depth.*—0.5 cm.

Sterile flower petals: Minute, irregular and malformed, less than 1 mm.

Sterile flower sepal:

*Arrangement.*—Whorl.

*Number.*—4 to 5.

*Shape.*—Broad deltate.

*Tip.*—Obtuse.

*Base.*—Rounded.

*Margin.*—Crenate.

*Length.*—5.3 mm.

*Width.*—4.9 mm.
*Texture, upper.*—Smooth, glabrous.
*Texture, lower.*—Smooth, glabrous.
*Color.*—Upper surface at first opening: Near RHS Red-Purple 69D. Upper surface at maturity: Near RHS Red-Purple 65D. Under surface at first opening: Near RHS Red-Purple 69D. Under surface at maturity: Near RHS Red-Purple 65D. Upper surface fading to: Near RHS White N155B. Lower surface fading to: Near RHS White N155B.

Sterile flower pedicel:
*Length.*—About 3 to 4 mm.
*Diameter.*—1.5 mm.
*Angle.*—0-45°.
*Strength.*—Soft.
*Texture.*—Smooth.
*Color.*—Near RHS Yellow-green 145C.

Fertile flower:
*Bud shape.*—Orbicular.
*Bud length.*—2.5 mm.
*Bud diameter.*—1 mm.
*Bud color.*—Near RHS Yellow-Green 145D flushed Red-Purple 69D.
*Flower aspect.*—outwardly facing.
*Flower shape.*—Irregular orbicular.
*Flower length.*—3 mm.
*Flower diameter.*—2 mm.
*Flower depth.*—2 mm.

Fertile flower petals:
*Length of petal.*—1.5 mm.
*Width of petal.*—1 mm.
*Apex.*—Rounded.
*Shape of petal.*—Orbicular.
*Petal margin.*—Entire.
*Petal arrangement.*—Whorl.
*Petal number.*—4 to 6.
*Petal base.*—Truncate.
*Petal texture.*—Smooth, glabrous, upper and under side.
*Color.*—Upper surface at first opening: Near Red-Purple 69D. Upper surface at maturity: Near Red-Purple 69D. Under surface at first opening: Near Yellow-Green 145D flushed Red-Purple 69D. Under surface at maturity: Near Red-Purple 69D. Upper surface fading to: Near RHS Near Red-Purple 69C. Lower surface fading to: Near Red-Purple 69D.

Fertile flower sepal:
*Arrangement.*—Single whorl.
*Number.*—5 to 7.
*Shape.*—Wide, rounded deltate.
*Tip.*—Broad acute.
*Base.*—Truncate.
*Margin.*—Entire.
*Length.*—1 mm.
*Width.*—0.75 mm.
*Texture, upper.*—Smooth, glabrous.
*Texture, lower.*—Smooth, glabrous.
*Color.*—Upper surface at first opening: Near RHS Yellow-Green 149D. Upper surface at maturity: Near RHS Yellow-Green 149D. Under surface at first opening: Near RHS Yellow-Green 149D. Under surface at maturity: Near RHS Red-Purple 69D. Upper surface fading to: Near RHS Yellow-Green 149D. Lower surface fading to: Near RHS Yellow-Green 149D.

Fertile flower pedicel:
*Angle.*—About 45° from attachment.
*Strength.*—Soft.
*Length.*—2 mm.
*Width.*—0.5 mm.
*Texture.*—Smooth.
*Color.*—Near RHS Yellow-green 149D flushed Red-Purple 69D.

Sterile flower sepal:
*Arrangement.*—Whorled, or semi-double whorled.
*Number.*—4 to 8.
*Shape.*—Wide deltate.
*Tip.*—Acute.
*Base.*—Truncate.
*Margin.*—Irregularly dentate and slightly undulate.
*Length.*—Outer whorl about 4 mm, inner whorl (when present) 2.5 mm.
*Width.*—Outer whorl about 3 mm, inner whorl (when present) 2 mm.
*Texture, upper.*—Smooth, glabrous.
*Texture, lower.*—Smooth, glabrous.
*Color.*—Upper surface at first opening: Near RHS Yellow-Green 145D. Upper surface at maturity: Near RHS Red-Purple 69D. Under surface at first opening: Near RHS Yellow-Green 145D. Under surface at maturity: Near RHS Red-Purple 69D. Upper surface fading to: Near RHS Red-Purple 69D. Lower surface fading to: Near RHS Red-Purple 69D.

Sterile flower pedicel:
*Angle.*—About 75° from attachment.
*Strength.*—Moderately strong.
*Length.*—3 mm.
*Width.*—2 mm.
*Texture.*—Glabrous.
*Color.*—Near RHS Red-Purple 69D.

REPRODUCTIVE ORGANS

Reproductive organs malformed, less than 1 mm.

OTHER CHARACTERISTICS

Disease resistance: Neither resistance nor susceptibility to diseases or pests has been observed in this variety.
Cold tolerance: −45° C. to 36° C.
Fruit/seed production: Not observed.

What is claimed is:

1. A new and distinct cultivar of *Hydrangea* plant named 'MONPULSEL' as herein illustrated and described.

* * * * *